US012629034B2

(12) United States Patent
Lee et al.

(10) Patent No.: US 12,629,034 B2
(45) Date of Patent: May 19, 2026

(54) ELECTRONIC DEVICE AND METHOD OF ESTIMATING CORE BODY TEMPERATURE USING THE SAME

(71) Applicants:SAMSUNG ELECTRONICS CO., LTD., Suwon-si (KR); INDUSTRY-ACADEMIC COOPERATION FOUNDATION, YONSEI UNIVERSITY, Seoul (KR)

(72) Inventors: Ho Taik Lee, Suwon-si (KR); Woochul Kim, Seoul (KR); Bok Soon Kwon, Suwon-si (KR); Sang Kyu Kim, Suwon-si (KR); Gimin Park, Suwon-si (KR); Sungho Kim, Suwon-si (KR); Jiyong Kim, Seoul (KR); Seungjai Woo, Seoul (KR); So Young Lee, Suwon-si (KR); Hong Soon Rhee, Suwon-si (KR)

(73) Assignees: SAMSUNG ELECTRONICS CO., LTD., Suwon-si (KR); INDUSTRY-ACADEMIC COOPERATION, YONSEI UNIVERSITY, Seoul (KR)

( * ) Notice: Subject to any disclaimer, the term of this patent is extended or adjusted under 35 U.S.C. 154(b) by 432 days.

(21) Appl. No.: 18/138,999

(22) Filed: Apr. 25, 2023

(65) Prior Publication Data

US 2024/0138682 A1 May 2, 2024

(30) Foreign Application Priority Data

Oct. 27, 2022 (KR) ........................ 10-2022-0140104
Dec. 30, 2022 (KR) ........................ 10-2022-0190434

(51) Int. Cl.
*A61B 5/01* (2006.01)
*A61B 5/00* (2006.01)

(52) U.S. Cl.
CPC .............. *A61B 5/01* (2013.01); *A61B 5/0008* (2013.01); *A61B 5/6802* (2013.01); *A61B 2562/0271* (2013.01)

(58) Field of Classification Search
CPC .. A61B 5/01; A61B 5/0008; A61B 2562/0271
See application file for complete search history.

(56) References Cited

U.S. PATENT DOCUMENTS

| 7,249,883 B2 | 7/2007 | Kuroda et al. |
| 7,299,090 B2 | 11/2007 | Koch |
| (Continued) | | |

FOREIGN PATENT DOCUMENTS

| CN | 113558582 A | 10/2021 |
| CN | 110840416 B | 6/2022 |
| (Continued) | | |

OTHER PUBLICATIONS

Feng et al., "Development of an improved wearable device for core body temperature monitoring based on the dual heat flux principle," Physiol. Meas. vol. 38, No. 652, 2017, Abstract only, Total 2 pages, DOI 10.1088/1361-6579/aa5f43.

(Continued)

*Primary Examiner* — Daniel L Cerioni
(74) *Attorney, Agent, or Firm* — Sughrue Mion, PLLC

(57) ABSTRACT

An electronic device may include: a first temperature sensor configured to measure a first temperature of a skin surface when a user comes into contact with a main body of the electronic device; a first heating element spaced apart from the first temperature sensor by a first predetermined distance; a second temperature sensor spaced apart from the first heating element by a second predetermined distance and configured to measure a second temperature inside the main body; and a processor configured to: estimate heat flux based on the first temperature and the second temperature; estimate (Continued)

a blood perfusion rate of the user based on a temperature of the first heating element and the first temperature, and estimate a core body temperature of a user based on the first temperature, the estimated heat flux, and the estimated blood perfusion rate.

11 Claims, 14 Drawing Sheets

(56) References Cited

U.S. PATENT DOCUMENTS

| | | | |
|---|---|---|---|
| 9,101,271 | B2 | 8/2015 | Sattler |
| 9,354,122 | B2 | 5/2016 | Bieberich et al. |
| 9,357,929 | B2 | 6/2016 | Paquet |
| 9,699,546 | B2 | 7/2017 | Qian et al. |
| 10,209,209 | B2 | 2/2019 | Ikeda et al. |
| 10,368,811 | B1 | 8/2019 | Bajaj et al. |
| 10,765,409 | B2 | 9/2020 | Lafon et al. |
| 11,109,764 | B2 | 9/2021 | Bongers et al. |
| 11,224,344 | B2 | 1/2022 | Ellis et al. |
| 11,406,326 | B2 | 8/2022 | Haber et al. |
| 2009/0306536 | A1* | 12/2009 | Ranganathan ........... A61B 5/01 |
| | | | 600/549 |
| 2014/0341599 | A1* | 11/2014 | Itoh .................... G03G 15/2039 |
| | | | 399/69 |
| 2018/0014734 | A1 | 1/2018 | Rogers et al. |
| 2019/0350462 | A1 | 11/2019 | Biederman et al. |
| 2019/0388031 | A1 | 12/2019 | Haber et al. |
| 2020/0060869 | A1 | 2/2020 | Telfort et al. |
| 2020/0217727 | A1 | 7/2020 | Heitz et al. |
| 2021/0038084 | A1 | 2/2021 | Dion et al. |
| 2021/0123819 | A1 | 4/2021 | Seyama et al. |
| 2021/0177272 | A1 | 6/2021 | Seyama et al. |
| 2022/0128413 | A1 | 4/2022 | Smits et al. |

FOREIGN PATENT DOCUMENTS

| | | | |
|---|---|---|---|
| JP | 5898204 | B2 | 4/2016 |
| WO | 2021/057873 | A1 | 4/2021 |

OTHER PUBLICATIONS

Gunga et al., "A non-invasive device to continuously determine heat strain in humans," Journal of Thermal Biology, vol. 33, No. 5, Jul. 2008, Abstract only, Total 2 pages, https://doi.org/10.1016/j.jtherbio.2008.03.004.

Malchaire et al., "Evaluation of the metabolic rate based on the recording of the heart rate," Industrial Health 2017, vol. 55, pp. 219-232, 2017.

Werner et al., "Temperature profiles with respect to inhomogeneity and geometry of the human body," Journal of Applied Physiology, Sep. 1988, Abstract only, Total 2 pages, https://doi.org/10.1152/jappl.1988.65.3.1110.

Communication dated Feb. 29, 2024, issued by the European Patent Office in counterpart European Application No. 23174787.4.

* cited by examiner

1300

ELECTRONIC DEVICE AND METHOD OF ESTIMATING CORE BODY TEMPERATURE USING THE SAME

CROSS-REFERENCE TO RELATED APPLICATION(S)

This application claims priority from Korean Patent Application No. 10-2022-0140104, filed on Oct. 27, 2022 and Korean Patent Application No. 10-2022-0190434, filed on Dec. 30, 2022, in the Korean Intellectual Property Office, the disclosures of which are incorporated herein by reference in their entireties.

BACKGROUND

1. Field

Apparatuses and methods consistent with example embodiments relate to estimating a user's core body temperature.

2. Description of the Related Art

Body temperature is a critical vital sign with important clinical significance. A body temperature sensor may be applied to various applications, such as checking infections in patients, monitoring thermal side effects of medications, or identifying the time of ovulation in women.

Body temperature sensors may be classified into contact and non-contact types. Examples of the contact type sensor may include a sensor for detecting a change in electrical resistance, such as a Resistance Temperature Detector (RTD), a thermistor, etc., a thermocouple for detecting electromotive force, and the like. Further, examples of the non-contact type sensor may include a thermopile, a microbolometer, etc., which measures body temperature by detecting infrared rays radiating from a body surface.

Core body temperature refers to body temperature of main internal organs, and remains constant unlike the skin temperature that varies greatly with environment factors such as atmospheric temperature. Measuring core body temperature may require multiple sensors to collect various data points. However, compact wearable devices have limited space, making it challenging to include multiple measurement sensors.

SUMMARY

According to an aspect of the present disclosure, an electronic device may include: a first temperature sensor configured to measure a first temperature of a skin surface of a user when the user comes into contact with a main body of the electronic device; a first heating element spaced apart from the first temperature sensor by a first predetermined distance; a second temperature sensor spaced apart from the first heating element by a second predetermined distance and configured to measure a second temperature inside the main body; and a processor configured to: estimate heat flux based on the first temperature and the second temperature; estimate a blood perfusion rate of the user based on a temperature of the first heating element and the first temperature, and estimate a core body temperature of the user based on the first temperature, the estimated heat flux, and the estimated blood perfusion rate.

The processor may be further configured to estimate the heat flux based on a difference between the first temperature and the second temperature.

By operating the first heating element, the processor may be further configured to estimate the blood perfusion rate based on a phase difference between the temperature of the first heating element and the first temperature.

The processor may be further configured to control an on state and an off state of the first heating element so that a temperature phase of the first heating element has a sine wave pattern over time.

The processor may be further configured to: estimate thermal contact resistance between the main body and the skin surface that is generated when the main body comes into contact with the skin surface; and correct the estimated blood perfusion rate based on the estimated thermal contact resistance.

The electronic device may further include a photoplethysmography (PPG) sensor configured to measure a PPG signal of the user, wherein the processor may be further configured to: estimate an amount of heat generation by metabolism based on the PPG signal; and estimate the core body temperature of the user based on the first temperature, the estimated heat flux, the estimated blood perfusion rate, and the estimated amount of heat generation.

The electronic device may further include a second heating element disposed between the first heating element and the second temperature sensor, wherein by operating the second heating element, the processor may be further configured to estimate, as the heat flux, power of the second heating element at a time when the first temperature and the second temperature become equal to each other.

Each of the first heating element and the second heating element may be formed in a multi-layer structure.

The processor may be further configured to operate the first heating element and the second heating element independently of each other.

At least one of the first temperature sensor and the second temperature sensor may be a contact type temperature sensor.

The first temperature sensor may be disposed at a center of a first end of the main body, and the second temperature sensor may be disposed at a center of a second end of the main body.

The electronic device may further include an output interface configured to provide the user with the estimated core body temperature of the user by a visual or non-visual method.

According to another aspect of the present disclosure, a method of estimating core body temperature by an electronic device, may include: by a first temperature sensor spaced apart from a first heating element by a first predetermined distance, measuring a first temperature of a skin surface of a user when the user comes into contact with a main body of the electronic device; by a second temperature sensor spaced apart from the first heating element by a second predetermined distance, measuring a second temperature inside the main body; estimating heat flux based on the first temperature and the second temperature; estimating a blood perfusion rate based on a temperature of the first heating element and the first temperature; and estimating a core body temperature of the user based on the first temperature, the estimated heat flux, and the estimated blood perfusion rate.

The estimating of the heat flux may include estimating the heat flux based on a difference between the first temperature and the second temperature.

The estimating of the blood perfusion rate may include estimating the blood perfusion rate based on a phase difference between the temperature of the first heating element and the first temperature.

The estimating of the blood perfusion rate may include: estimating thermal contact resistance between the main body and the skin surface that is generated when the main body comes into contact with the skin surface; and correcting the estimated blood perfusion rate based the estimated thermal contact resistance.

The estimating of the core body temperature of the user may include: estimating an amount of heat generation by metabolism based on a photoplethysmography (PPG) signal obtained by a PPG sensor; and estimating the core body temperature of the user based on the first temperature, the estimated heat flux, the estimated blood perfusion rate, and the estimated amount of heat generation.

The method may further include, by an output interface, providing the user with the estimated core body temperature of the user by a visual or non-visual method.

A wearable device may include: a main body; a strap connected to the main body; a first temperature sensor configured to measure a first temperature of a skin surface of a user when the user comes into contact with the main body of the wearable device; a second temperature sensor configured to measure a second temperature inside the main body; a plurality of heating elements disposed between the first temperature sensor and the second temperature sensor; and a processor configured to: estimate heat flux and a blood perfusion rate by operating the plurality of heating elements; and estimate a core body temperature of the user based on the first temperature, the estimated heat flux, and the estimated blood perfusion rate.

The wearable device may include a photoplethysmography (PPG) sensor configured to measure a PPG signal of the user, wherein the processor may be further configured to: estimate an amount of heat generation by metabolism based on the PPG signal, and estimate the core body temperature of the user based on the first temperature, the estimated heat flux, the estimated blood perfusion rate, and the estimated amount of heat generation.

BRIEF DESCRIPTION OF THE DRAWINGS

The above and/or other aspects will be more apparent by describing certain example embodiments, with reference to the accompanying drawings, in which.

DETAILED DESCRIPTION

Figure 1:
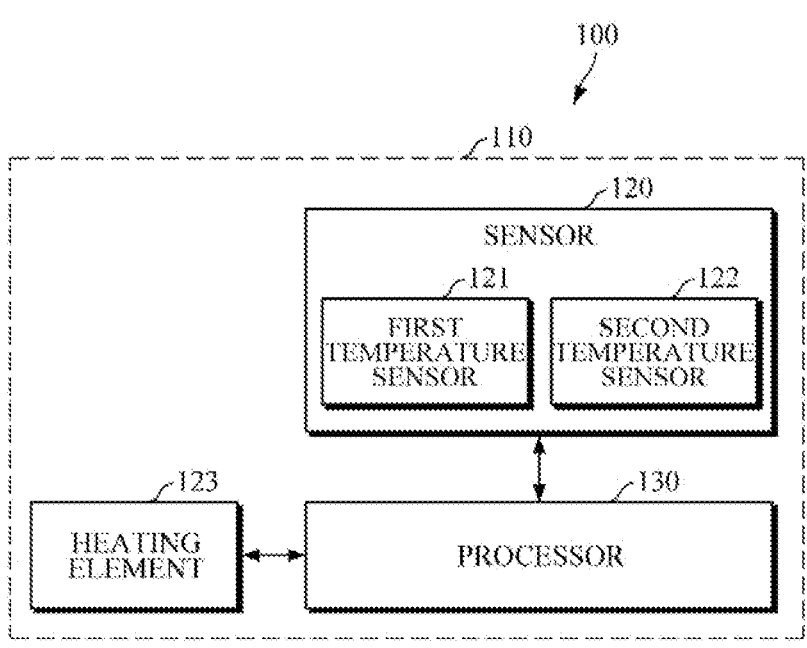
FIG. 1 is a block diagram illustrating an electronic device according to an embodiment of the present disclosure.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms "first," "second," etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'unit' or 'module', etc., should be understood as a unit that performs at least one function or operation and that may be embodied as hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

An electronic device according to various embodiments of the present disclosure which will be described below may include, for example, at least one of a wearable device, a smartphone, a tablet PC, a mobile phone, a video phone, an electronic book reader, a desktop computer, a laptop computer, a netbook computer, a workstation, a server, a PDA, a portable multimedia player (PMP), an MP3 player, a medical device, and a camera. The wearable device may include at least one of an accessory type wearable device (e.g., wristwatch, ring, bracelet, anklet, necklace, glasses, contact lens, or head mounted device (HMD)), a textile/clothing type wearable device (e.g., electronic clothing), a body-mounted type wearable device (e.g., skin pad or tattoo), and a body implantable type wearable device. However, the wearable device is not limited thereto and may include, for example, various portable medical measuring devices (antioxidant measuring device, blood glucose monitor, heart rate monitor, blood pressure measuring device, thermometer, etc.), magnetic resonance angiography (MRA), magnetic resonance imaging (MRI), computed tomography (CT), imaging system, ultrasonic system, etc.), and the like. However, the electronic device is not limited to the above devices.

Figure 2:
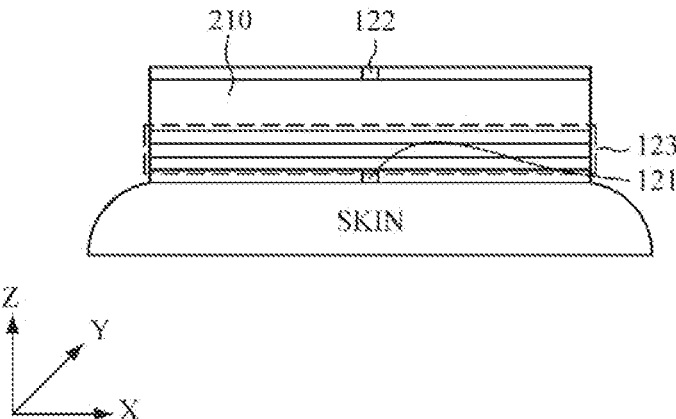
FIG. 2 is a diagram illustrating an example of a structure of an electronic device.

FIG. 1 is a block diagram illustrating an electronic device according to an embodiment of the present disclosure. FIG. 2 is a diagram illustrating an example of a structure of an electronic device.

Referring to FIG. 1, an electronic device 100 includes a sensor 120, a heating element 123, and a processor 130 in a main body 110. The sensor 120 may include a plurality of temperature sensors, and the processor 130 may estimate a user's core body temperature by using data obtained by the sensor 120 and the heating element 123.

The sensor 120 may include a first temperature sensor 121 configured to measure a first temperature of a skin surface when an object comes into contact with the main body, and a second temperature sensor 122 spaced apart from the heating element 123 by a predetermined distance (e.g., within 5 mm) and configured to measure a second temperature inside the main body. The object may be a body part where the core body temperature may be easily measured, such as an area adjacent to the radial artery on the wrist, an upper part of the wrist where capillary blood or venous blood passes, or a peripheral part of the body, such as toes and the like, and may also be the ears, forehead, chest, and other areas.

The first temperature sensor 121 and the second temperature sensor 122 may be disposed at different positions in the main body 110. For example, the first temperature sensor 121 may be disposed at the center of a first end of the main body 110 (e.g., lower surface or a position within a predetermined distance above the lower surface), and the second temperature sensor 122 be disposed at the center of a second end of the main body 110 (e.g., upper surface or a position within a predetermined distance below the upper surface). In this case, the first temperature sensor 121 and the second temperature sensor 122 may face each other. In addition, the first temperature sensor 121 and/or the second temperature sensor 122 may be a contact type temperature sensor, such as a thermistor, and may also include a temperature sensor such as a digital temperature sensor, thermopile, and the like. The type of temperature sensor is not limited thereto sensor.

The heating element 123 may generate heat in the electronic device 100, and may take the form of a heater or a similar structure. In addition, a heating structure (e.g., battery) already included in the electronic device 100 may be used a heater, and an LED capable of light-to-heat-conversion may also be used. The type of the heating element 123 is not limited thereto. Further, the heating element 123 may be spaced apart by a predetermined distance (e.g., within 3 mm) from the first temperature sensor 121 toward the top of the main body, and may also be disposed in contact with the top of the first temperature sensor 121. The position of the heating element 123 is not limited thereto.

Figure 3:
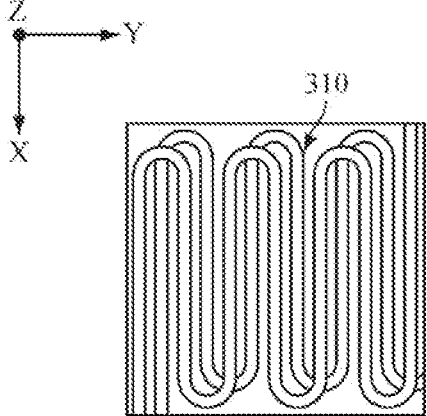
FIG. 3 is a diagram illustrating a structure of a heating element.

FIG. 3 is a diagram illustrating a structure of the heating element 123.

Referring to FIG. 3, the heating element 123 may be formed of multiple layers. The heating element 123 may be implemented as a multiple-layered serpentine heater with a meandering pattern. For example, the heating element 123 may be formed with two layers that are alternately arranged (310) to produce heat uniformly, and these layers may be connected together in series. The two layers may be stacked in a thickness direction of the heating element 123 (or the thickness direction of the main body 110). The heating element 123 may have an alternate arrangement (310) for uniform heat generation and may be integrally connected to each other. In addition, the heating element 123 may have a width and a length of 10 mm or less.

Referring back to FIG. 2, the electronic device 100 may further include a thermally low conductive material 210 between the heating element 123 and the second temperature sensor 122. For example, the first temperature sensor 121, the heating element 123, the thermally low conductive material 210, and the second temperature sensor 122 may be formed in a stacked structure from bottom to top. The thermally low conductive material 210 may be a dielectric material that has a high electrical and thermal resistance and provides electrical and thermal insulation. The thermally low conductive material 210 may be an insulator having a size of, for example, 0.1 mm to 5 mm and may be a material (e.g., polyurethane foam) having a thermal conductivity of 0.1 W/mK or less. However, the size and thermal conductivity of the thermally low conductive material 210 are not limited thereto. In addition, an air-filled structure may also be implemented without incorporating a separate material between the heating element 123 and the second temperature sensor 122.

The main body 110 may be, for example, of a wearable type which may be worn on a user's body part (e.g., wrist), and may be a smartphone type device which may be carried by a user.

The processor 130 may be electrically connected to the sensor 120 and the heating element 123 and may control the sensor 120 and the heating element 123 during estimation of a user's core body temperature. The processor 130 may estimate the user's core body temperature based on data obtained by the sensor 120. For example, the processor 130 may estimate heat flux based on the first temperature and the second temperature, may estimate a blood perfusion amount or a blood perfusion rate by operating the heating element 123, and may estimate the user's core body temperature based on the first temperature, the estimated heat flux, and the estimated blood perfusion amount or the estimated blood perfusion rate.

First, the processor 130 may estimate the heat flux based on a first temperature of a skin surface which is measured by the first temperature sensor 121, and a second temperature inside the main body which is measured by the second temperature sensor 122. The processor 130 may estimate the heat flux based on a difference between the first temperature and the second temperature, and also based on the thickness and thermal conductivity of the thermally conductive material, which may be represented by the following Equation 1.

$$q'' = \frac{k}{l}(T_1 - T_2)$$ [Equation 1]

Herein, q" denotes the heat flux, k denotes the thermal conductivity of the thermally conductive material, and l denotes the thickness of the thermally conductive material. In this case, the thermally conductive material may be air, and the thermal conductivity k of air and a distance between the heating element 123 and the second temperature sensor 122 may be used as the value of l.

In addition, the processor 130 may estimate the heat flux by directly using the difference between the first temperature and the second temperature. For example, the processor 130 may determine the heat flux, corresponding to the difference between the first temperature and the second temperature, by using a prestored model that defines a relationship between the heat flux and the difference between the first temperature and the second temperature.

In another example, the electronic device 100 may further include a heating element in the main body, and the processor may also estimate the heat flux by using the included heating element.

Figure 4:
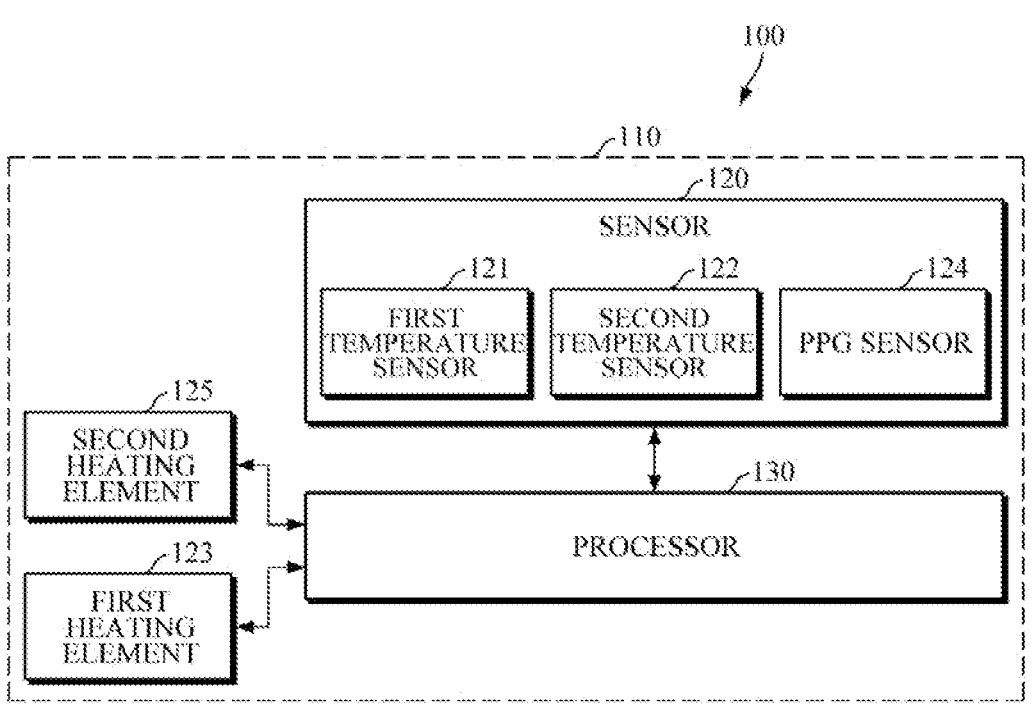
FIG. 4 is a block diagram illustrating an electronic device according to another embodiment of the present disclosure.
Figure 5:
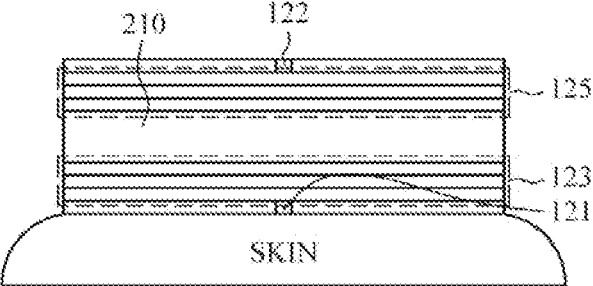
FIG. 5 is a diagram illustrating another example of a structure of an electronic device.

FIG. 4 is a block diagram illustrating an electronic device according to another embodiment of the present disclosure, and FIG. 5 is a diagram illustrating another example of a structure of an electronic device.

Referring to FIGS. 4 and 5, the electronic device 100 may further include a second heating element 125 between the heating element 123 and the second temperature sensor 122. The second heating element 125 may be disposed, for example, on a lower contact surface of the second temperature sensor 122. By operating the second heating element 125, the processor 130 may estimate, as the heat flux, power (W/m²) of the second heating element 125 at a time when the first temperature and the second temperature become equal to each other. For example, when the processor 130 operates the second heating element 125, and the first temperature and the second temperature become equal to each other, thermal equilibrium is reached between heat flux from the core to the skin surface and heat flux from the second heating element 125 to the skin surface, resulting in zero heat flux, and may estimate the heat flux at the time based on power of the second heating element 125. In order to accurately estimate the heat flux, the first temperature sensor 121, the second heating element 125, and the second temperature sensor 122 may be arranged in series on the same line.

Then, by operating the first heating element 123, the processor 130 may estimate a blood perfusion rate based on a phase difference between temperature of the first heating element 123 and the first temperature. The temperature of the first heating element 123 may be determined using a temperature sensor that measures the temperature of the first heating element 123, or without a temperature sensor by using a temperature control module of the processor 130. For example, the temperature control module may adjust an on/off time of the first heating element 123 and/or an amount of power supply to the first heating element 123 according to a target temperature that is set for the first heating element 123. In such a case, the target temperature may be used as the temperature of the first heating element 123. The blood perfusion rate may be computed based on the following Equation 2. Generally, the perfusion amount refers to an amount of blood flow per minute in blood vessels.

$$\omega_b = -\frac{\rho c_p \omega}{\tan(2\varphi)\rho_b c_{pb}} \qquad \text{[Equation 2]}$$

Herein, $\omega_b$ denotes the blood perfusion rate, $\rho$ denotes the subcutaneous tissue, e.g., the density of adipose tissue, $\rho_L$ denotes the density of blood, $c_p$ denotes specific heat at constant pressure of the subcutaneous tissue, $c_{pb}$ denotes specific heat at constant pressure of blood, $\omega$ denotes a predetermined frequency of a heater, and $\varphi$ denotes the phase difference between the temperature of the first heating element 123 and the first temperature, in which $\rho$, $\rho_b$, $c_p$, and $c_{pb}$ may be predetermined common values.

The processor 130 may control an on/off state of the first heating element 123 so that the temperature phase of the first heating element 123 may exhibit a sine wave pattern over time. For example, when the processor 130 operates the first heating element 123 so that the temperature phase over time has a sine wave pattern, the first temperature, which is the temperature of the skin surface, also has the sine wave pattern and follows the phase of the first heating element 123, thereby causing a phase difference between the temperature of the first heating element 123 and the temperature of the first temperature. The blood perfusion rate may be obtained by substituting the generated phase difference $\varphi$ into the above Equation 2.

The processor 130 may adjust a frequency of the first heating element 123 based on a user's selection, thereby selecting a body part, from which the blood perfusion rate is to be obtained, among body parts (e.g., dermis layer, subcutaneous adipose layer, and muscle layer).

Figure 6:
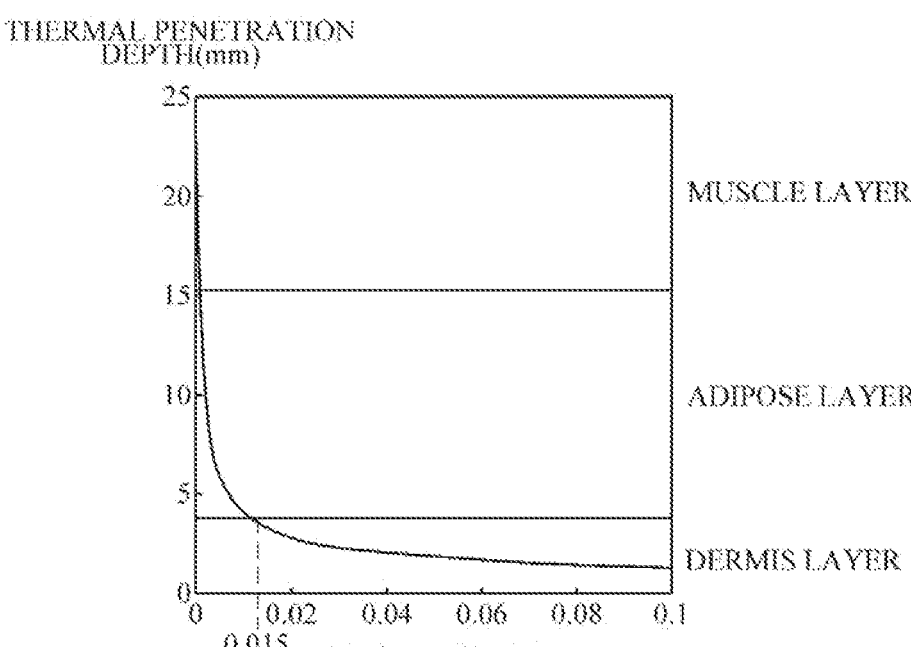
FIG. 6 is a graph showing a relationship between a frequency of a heating element and thermal penetration depth.

FIG. 6 is a graph showing a relationship between a frequency of a heating element and thermal penetration depth.

Referring to FIG. 6, it can be seen that in order to obtain a blood perfusion rate of a body part located relatively deep inside the body, such as the adipose layer or the muscle layer, it is required to reduce a driving frequency of the heating element to, for example, 0.015 Hz or less; and in order to obtain a blood perfusion rate of a body part located at a relatively shallow depth, such as the dermis layer, it is required to increase a driving frequency of the heating element to, for example, 0.015 Hz or more.

In addition, the processor 130 may estimate thermal contact resistance generated when the main body 110 comes into contact with the skin surface, and may correct the blood perfusion rate based on an estimation result.

Thermal contact resistance is a phenomenon in which thermal resistance significantly increases at the interface of two contacting materials in physical contact when heat flows through the materials. The thermal contact resistance may be obtained by dividing a temperature difference between two objects by heat flux. For example, thermal contact resistance may occur when the main body 110 of the electronic device 100 comes into contact with a skin surface (e.g., wrist), and the thermal contact resistance may affect the accuracy of the estimated blood perfusion rate. Accordingly, the processor 130 may correct the estimated blood perfusion rate by estimating thermal contact resistance between the main body 110 and the skin surface. For example, the processor may calculate, for example, a mean value or standard deviation of thermal contact resistance for a plurality of periods by changing the frequency of the heating element, and may correct the estimated blood perfusion rate by using the calculated mean value or standard deviation as a correction value.

In one embodiment, the processor 130 may operate the first heating element 123 and the second heating element 125 independently of each other to reduce interference between the heat generated by the first heating element 123 and the second heating element 125. For example, when estimating the blood perfusion rate, the processor 130 may operate only the first heating element 123 without operating the second heating element 125, and when estimating the heat flux, the processor 130 may operate only the second heating element 125 without operating the first heating element 123. The operation of the heating elements by the processor 130 is not limited thereto.

Then, the processor 130 may estimate a user's core body temperature based on the first temperature, the estimated heat flux, and the estimated blood perfusion rate. In this case, the electronic device 100 may further include a pulse wave sensor (e.g., photoplethysmography (PPG) sensor) for measuring a pulse wave signal of an object. For example, the processor 130 may further estimate an amount of heat generation by metabolism based on a PPG signal obtained by the PPG sensor, and may estimate a user's core body temperature based on the first temperature, the estimated heat flux, the estimated blood perfusion rate, and the estimated amount of heat generation.

First, the processor 130 may estimate the amount of heat generation by metabolism in a user's body based on the user's heart rate, age, height, weight, and the like.

For example, the processor 130 may estimate the amount of heat generation by the user's metabolism based further on the heart rate in addition to age, height, and weight. In this case, the heart rate may be input by the user, may be received from an external device, or may be estimated by extracting the heart rate from the PPG signal measured by the PPG sensor 124.

The processor 130 may estimate the amount of heat generation by the user's metabolism by using a known relational expression with variables, such as the equivalent metabolic rate, Maximum Work Capacity (MWC), resting metabolism, average heart rate (HR), a user's gender, age, height, weight, and the like.

In another example, the processor 130 may also estimate a basal metabolic rate by using a known relational expression for estimating a basal metabolic rate based on age, height, and weight. The processor 130 may estimate an amount of heat generation by the user's metabolism based on a value obtained by multiplying the estimated basal metabolic rate by a predetermined constant depending on the user's amount of activity, e.g., the number of times of exercise, moving distance, and the like.

However, without estimating the amount of heat generation by the user's metabolism, the processor 130 may receive an amount of heat generation by the user's metabolism, which is estimated by an external device, through a communication interface and the like that communicate with the external device, or may receive an amount of heat generation which is previously input by a user.

Then, the processor 130 may estimate the user's core body temperature by applying the first temperature $T_1$, the estimated heat flux q", the estimated blood perfusion rate $\omega_b$, and the estimated amount of heat generation to a human heat model, which may be represented by the following Equations 3 and 4.

$$T_{core} = T_1 + q'' \frac{I_0(\sqrt{a}R)}{I_1(\sqrt{a}R)} \frac{1}{k\sqrt{a}} - \frac{q'''}{ka} \qquad \text{[Equation 3]}$$

$$a = \frac{\omega_b \rho_b C_{pb}}{k} \qquad \text{[Equation 4]}$$

Herein, $T_{core}$ denotes the core body temperature, and k denotes thermal conductivity of, for example, a user's wrist tissue and may be a predetermined common value or may be defined differently for each user's characteristics. In this case, the user's wrist tissue may include muscle, fat, bone, skin, and the like. In addition, q''' denotes the amount of heat generation, R denotes a radius of the user's wrist, and $I_0$ and $I_1$ denote the Bessel function which is a solution of heat transfer differential equation.

Generally, various measured values are required in order to measure the core body temperature. However, due to the limited structure of the wearable device, it may be challenging to mount all sensors for obtaining the required measured values in the main body. The embodiment of the present disclosure has effects in that the device may be manufactured in a compact size by reducing the number of sensors, and the core body temperature may be estimated using a human heat model, thereby increasing the accuracy of estimation.

Figure 7:
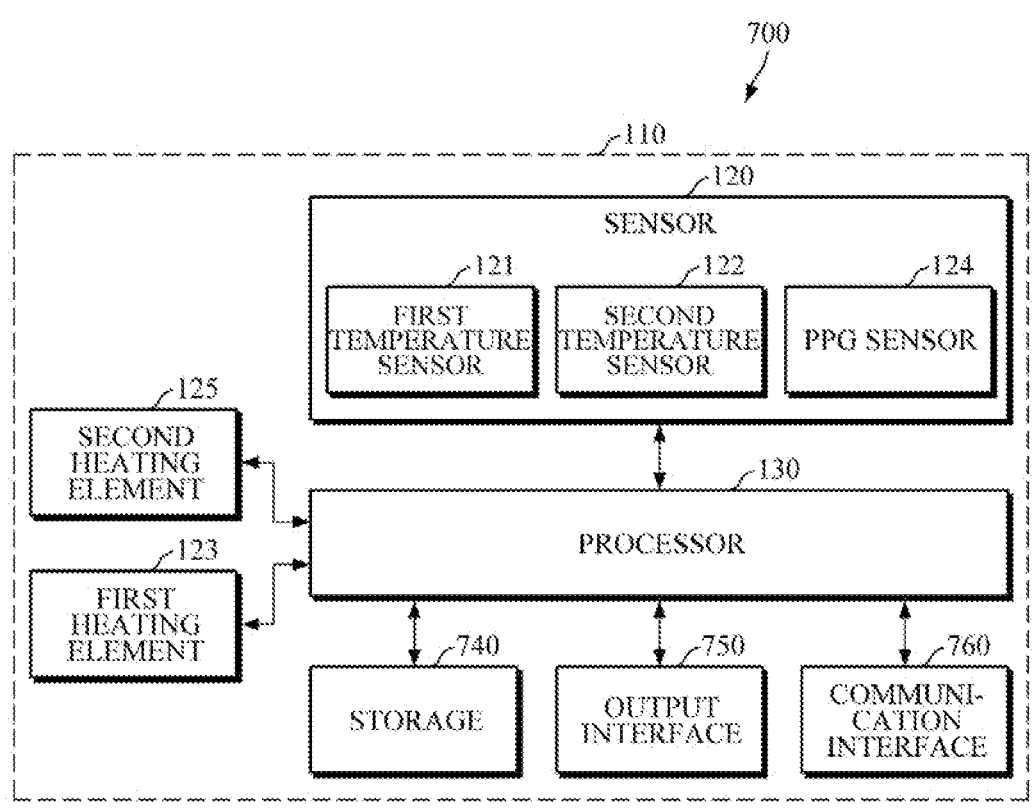
FIG. 7 is a block diagram illustrating an electronic device according to another embodiment of the present disclosure.

FIG. 7 is a block diagram illustrating an electronic device according to another embodiment of the present disclosure.

Referring to FIG. 7, an electronic device 700 includes, in the main body 110, the sensor 120 including the first temperature sensor 121, the second temperature sensor 122, and the PPG sensor 124, the first heating element 123, the second heating element 125, the processor 130, a storage 740, an output interface 750, and a communication interface 760. In this case, the sensor 120, the first heating element 123, the second heating element 125, and the processor 130 are the same as those in the embodiments of FIGS. 1 and 4, such that a detailed description thereof will be omitted.

The storage 740 may store information related to estimating core body temperature. For example, the storage 740 may store temperature data obtained by the sensor 120, thickness and thermal conductivity of a thermally conductive material, a selected frequency of the heating element, and processing results of the processor 130 such as heat flux, blood perfusion rate, amount of heat generation, and the like.

The storage 740 may include a storage medium having at least one type of a flash memory type, a hard disk type, a multimedia card micro type, a card type (e.g., a SD memory, a XD memory, etc.), a random access memory (RAM), a static random access memory (SRAM), a read-only memory (ROM), an electrically erasable programmable read-only memory (EEPROM), a programmable read-only memory (PROM), a magnetic memory, a magnetic disc, or an optical disc, etc., but is not limited thereto.

The output interface 750 may provide the processing results of the processor 130 to a user. For example, the processor 130 may provide the estimated core body temperature of the user by a visual or non-visual method.

The output interface 750 may include a display to show a core body temperature value that is estimated by the processor 130. If the estimated core body temperature value falls outside a (predetermined) normal range, the output interface 750 may provide a user with a warning message, by changing color or line thickness, or by displaying the abnormal value along with the normal range, so that the user may easily recognize and response to the abnormal core body temperature value.

Further, along with or without the information visually displayed on the display, the output interface 750 may provide the user with the estimated core body temperature value in a non-visual manner by voice, vibrations, tactile sensation, and the like using an audio output module such as a speaker and the like, or a haptic module.

The display may include touch circuitry adapted to detect a touch, and/or sensor circuitry (e.g., pressure sensor, etc.) adapted to measure the intensity of force incurred by the touch. An audio module may convert a sound into an electrical signal or vice versa. The audio module may obtain the sound via the input device, or may output the sound via the sound output device, and/or a speaker and/or a headphone of another electronic device directly or wirelessly connected to the electronic device. A haptic module may convert an electrical signal into a mechanical stimulus (e.g., vibration, motion, etc.) or electrical stimulus which may be recognized by a user by tactile sensation or kinesthetic sensation. The haptic module may include components such as a motor, a piezoelectric element, and/or an electric stimulator.

Figure 8A:
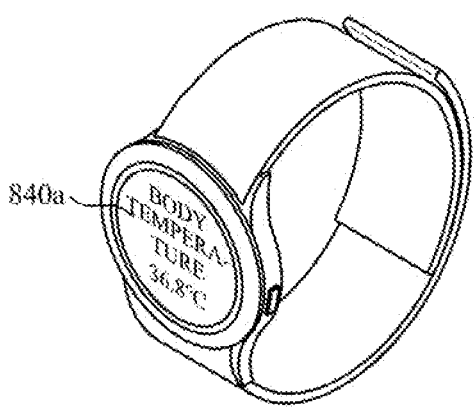
FIGS. 8A and 8B are diagrams illustrating an example of displaying core body temperature information on a display of an electronic device according to an embodiment of the present disclosure.
Figure 8B:
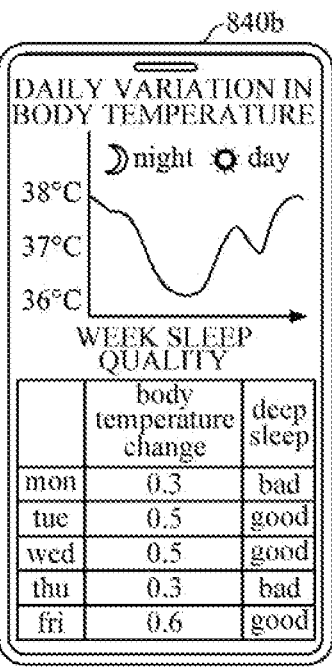

FIGS. 8A and 8B are diagrams illustrating an example of displaying core body temperature information on a display of the electronic device 700.

Referring to FIGS. 8A and 8B, a display 840*a* may be disposed on a front surface of a wearable device and may display an estimated core body temperature value. A display 840*b* may be disposed on a front surface of a smart device and may display an estimated core body temperature value, a change of core body temperature during a day, sleep quality related to the estimated core body temperature, and the like. In this case, the smart device may interwork with another external electronic device, e.g., wristwatch wearable device, ear-wearable device, etc., to estimate core body temperature based on data measured by a sensor part of the external electronic device, and may display the estimated core body temperature value on the display 840*b*. However, the output of the core body temperature value on the displays 840*a* and 840*b* is not limited thereto and may vary.

Referring back to FIG. 7, the communication interface 760 may communicate with an external device to transmit and receive various data related to estimating core body temperature. The external device may include an information processing device, such as a smartphone, a tablet PC, a desktop computer, a laptop computer, and the like. For example, the communication interface 760 may transmit a core body temperature estimation result to the external device, such as a smartphone and the like, and a user may monitor the estimated core body temperature over time by using the smartphone.

The communication interface 760 may communicate with the external device by using various wired and wireless communication techniques including Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, third generation (3G), fourth generation (4G), fifth generation (5G), and sixth generation (6G) communications, and the like. However, the communication techniques are not limited thereto.

Figure 9:
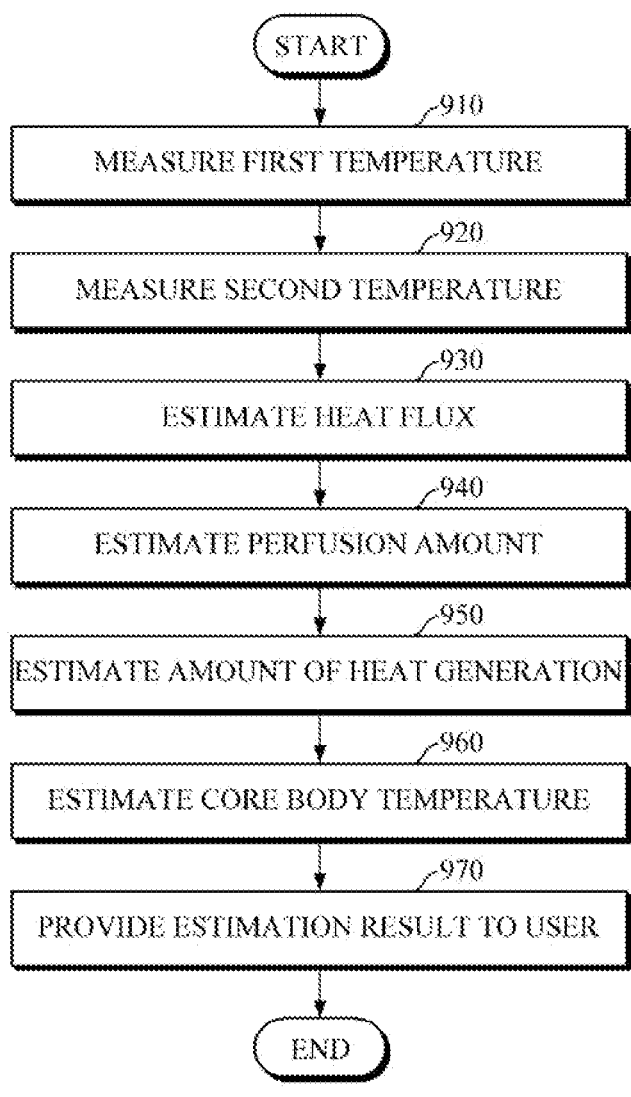
FIG. 9 is a flowchart illustrating a method of estimating core body temperature according to an embodiment of the present disclosure.

FIG. 9 is a flowchart illustrating a method of estimating core body temperature according to an embodiment of the present disclosure.

The method of FIG. 9 is an example of a method of estimating core body temperature by the electronic device 100 according to the embodiments of FIGS. 1 and 4, which are described above, and thus the method will be briefly described below in order to avoid redundancy.

Referring to FIG. 9, the electronic device may first measure a first temperature of a skin surface in operation 910 by using the first temperature sensor when an object comes into contact with the main body, and may measure a second temperature inside the main body in operation 920 by using the second temperature sensor disposed further away from the first temperature sensor than the first heating element spaced apart from the first temperature sensor by a predetermined distance.

Then, the electronic device may estimate heat flux based on the first temperature and the second temperature in operation 930. In this case, in the estimating of the heat flux, the electronic device may estimate the heat flux based on a difference between the first temperature and the second temperature and the thickness and thermal conductivity of a thermally conductive material. In addition, the electronic device may also estimate the heat flux by directly using the difference between the first temperature and the second temperature, and may further include another thermally conductive material to estimate the heat flux by using the included thermally conductive material.

Subsequently, the electronic device may estimate a blood perfusion rate by operating the first heating element in operation 940. In this case, the electronic device may estimate the blood perfusion rate based on a phase difference between the temperature of the first heating element and the first temperature, may estimate thermal contact resistance generated when the main body comes into contact with the skin surface, and may correct the estimated blood perfusion rate based on a result of the thermal contact resistance estimation.

Next, the electronic device may estimate an amount of heat generation by metabolism based on, for example, a PPG signal obtained by a pulse wave sensor (e.g., PPG sensor) in operation 950, and may estimate a user's core body temperature based on the first temperature, the estimated heat flux, the estimated blood perfusion rate, and the estimated amount of heat generation in operation 960. In this case, the electronic device may estimate the user's core body temperature by applying the first temperature, the estimated heat flux, the estimated blood perfusion rate, and the estimated amount of heat generation to a human heat model.

Then, the electronic device may provide a result of the estimated core body temperature to the user by a visual or non-visual method in operation 970. For example, the electronic device may display the estimated core body temperature value on the display. In this case, if the estimated core body temperature value falls outside a normal range, the electronic device may provide a user with information, such as warning, by changing color, line thickness, etc., or by displaying the abnormal value along with the normal range, so that the user may easily recognize the estimated value.

FIGS. 10 to 13 are diagrams illustrating examples of structures of an electronic device for estimating core body temperature. Examples of the electronic device may include not only a smartwatch, but also a smartphone, a smart band, smart glasses, a smart necklace, and an ear-wearable device, but the electronic device is not limited thereto.

Figure 10:
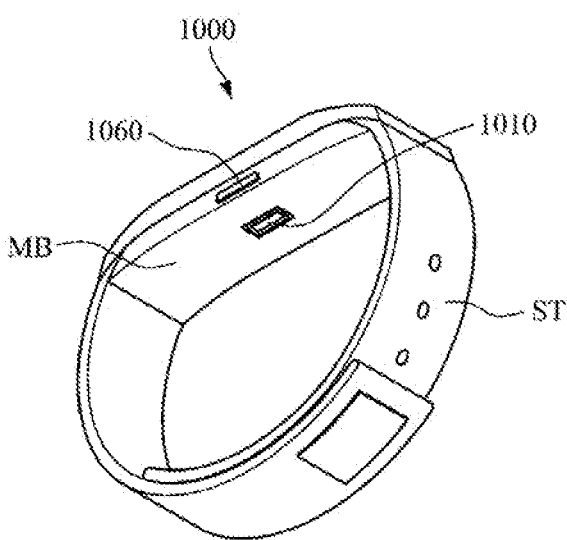
FIGS. 10 to 13 are diagrams illustrating examples of structures of an electronic device for estimating core body temperature.

Referring to FIG. 10, the electronic device may be implemented as a smart watch-type wearable device 1000 which includes a main body MB and a wrist strap ST.

The main body MB may be formed in various shapes. A battery may be embedded in the main body MB and/or the strap ST to supply power to various components of the wearable device. The strap ST may be connected to both ends of the main body to allow the main body to be worn on a user's wrist, and may be flexible so as to be wrapped around the user's wrist. The strap ST may be composed of a first strap and a second strap which are separated from each other. One ends of the first strap and the second strap are connected to both sides of the main body MB, and the other ends thereof may be connected to each other via a fastening means. In this case, the connecting means may be formed as magnetic fastening, Velcro fastening, pin fastening, and the like, but is not limited thereto. Further, the strap ST is not limited thereto, and may be integrally formed as a non-detachable band.

The main body MB may include a sensor 1010, a processor, a heating element, an output interface, a storage, a communication interface, and the like. However, depending on the size and shape of a form factor and the like, some of the display, the storage, and the communication interface may be omitted.

A manipulator 1060 may be formed on a side surface of the main body MB, as illustrated herein. The manipulator 1060 may receive a user command and may transmit the received command to the processor. In addition, the manipulator 1060 may have a power button to turn on/off the wearable device 1000.

The sensor 1010 may include temperature sensors disposed at different positions and attached to a structure in the main body. For example, a smartwatch may include a first temperature sensor for measuring a first temperature of a skin surface when an object comes into contact with the main body, and a second temperature sensor for measuring a second temperature inside the main body. In addition, a plurality of heating elements may be disposed between the first temperature sensor and the second temperature sensor in the main body.

The processor mounted in the main body MB may be electrically connected to various components as well as the sensor 1010. For example, when the strap is wrapped around a user's wrist and the main body is worn on the wrist, the processor may estimate heat flux and a blood perfusion rate by operating the plurality of heating elements, and may estimate the user's core body temperature based on the first temperature, the estimated heat flux, and the estimated blood perfusion rate. In this case, the sensor 101 may further include a PPG sensor for measuring a PPG signal of the object, and the processor may estimate an amount of heat generation by metabolism based on the PPG signal obtained by the PPG sensor, and may estimate the user's core body temperature based on the first temperature, the estimated heat flux, the estimated blood perfusion rate, and the estimated amount of heat generation.

Figure 11:
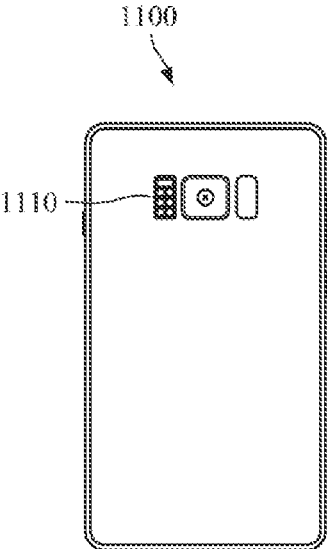

Referring to FIG. 11, the electronic device may be implemented as a mobile device 1100 such as a smartphone.

The mobile device 1100 may include a housing and a display panel. The housing may form the exterior of the mobile device 1100. The housing has a first surface, on which a display panel and a cover glass may be disposed sequentially, and the display panel may be exposed to the outside through the cover glass. A sensor 1110, heating elements, a camera module and/or an infrared sensor, and the like may be disposed on a second surface of the housing.

For example, a plurality of sensors for obtaining data from a user may be disposed on a rear surface of the mobile device 1100, and a fingerprint sensor disposed on the front surface thereof, a power button or a volume button disposed on a side surface thereof, sensors disposed on other positions of the front and rear surfaces thereof, and the like may be provided to estimate a user's core body temperature.

In addition, when a user transmits a request for measuring the core body temperature by executing an application and the like installed in the mobile device 1100, the mobile device 1100 may obtain data by using the sensor 1110 and heating elements, may measure the core body temperature by using the processor in the mobile device 1100, and may provide the user with the measured value and guidance information related to the core body temperature through a display.

Figure 12:
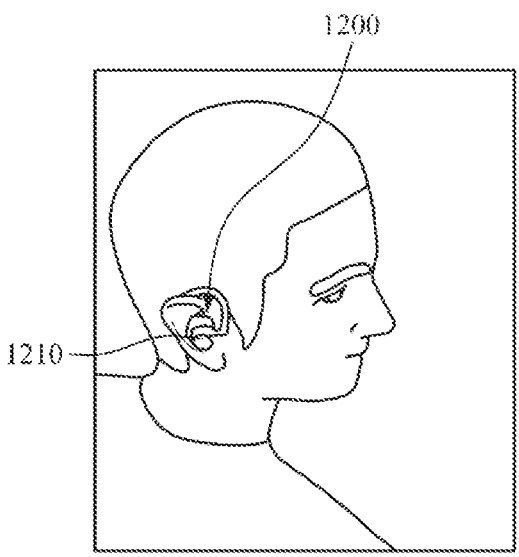

Referring to FIG. 12, the electronic device may also be implemented as an ear-wearable device 1200.

The ear-wearable device 1200 may include a main body and an ear strap. A user may wear the ear-wearable device 1200 by hanging the ear strap on the user's auricle. The ear strap may be omitted depending on the shape of ear-wearable device 1200. The main body may be inserted into the external auditory meatus. A sensor 1210 and a heating element may be mounted in the main body. The ear-wearable device 1200 may provide a user with a core body temperature measurement result and/or core body temperature guidance information as sound, or may transmit the information to an external device, e.g., a mobile device, a tablet PC, a personal computer, etc., through a communication module provided in the main body.

Figure 13:
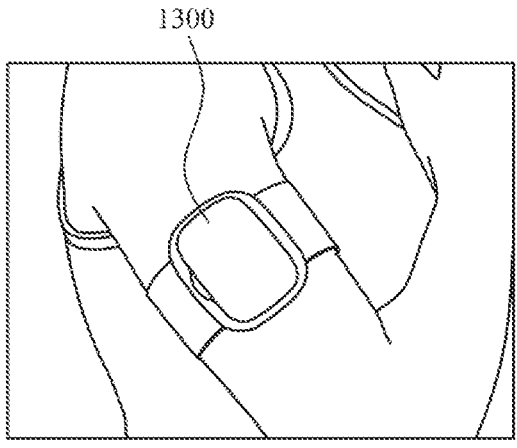

Referring to FIG. 13, an electronic device 1300 may be implemented as a patch-type device.

For example, the electronic device 1300 may be fixed to a body measurement location (e.g., upper arm) by a strap, to measure a user's core body temperature. In this case, the electronic device 1300 may provide the user with an estimated body temperature as sound or through a display, or may transmit the estimated body temperature to an external device, e.g., a mobile device, a tablet PC, a personal computer, another medical device, etc., through a communication module provided in the electronic device 1300.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An electronic device comprising:
   a first temperature sensor configured to measure a first temperature of a skin surface of a user when the user comes into contact with a main body of the electronic device;
   a second temperature sensor configured to measure a second temperature inside the main body;
   a first heating element disposed between the first temperature sensor and the second temperature sensor, and disposed closer to the first temperature sensor than to the second temperature sensor;
   a second heating element disposed between the first heating element and the second temperature sensor, and disposed closer to the second temperature sensor than to the first temperature sensor;
   an insulator disposed between the first heating element and the second heating element; and
   a processor configured to:
   estimate heat flux based on the first temperature and the second temperature by operating the second heating element;

estimate a blood perfusion rate of the user based on a temperature of the first heating element and the first temperature, and estimate a core body temperature of the user based on the first temperature, the estimated heat flux, and the estimated blood perfusion rate, wherein the first heating element and the second heating element comprise at least one of a heater, a battery, or a light emitting element (LED), wherein by operating the second heating element, the processor is further configured to estimate, as the heat flux, power of the second heating element at a time when the first temperature and the second temperature become equal to each other.

2. The electronic device of claim 1, wherein the processor is further configured to estimate the heat flux based on a difference between the first temperature and the second temperature.

3. The electronic device of claim 1, wherein by operating the first heating element, the processor is further configured to estimate the blood perfusion rate based on a phase difference between the temperature of the first heating element and the first temperature.

4. The electronic device of claim 3, wherein the processor is further configured to control an on state and an off state of the first heating element so that a temperature phase of the first heating element has a sine wave pattern over time.

5. The electronic device of claim 3, wherein the processor is further configured to:

estimate thermal contact resistance between the main body and the skin surface that is generated when the main body comes into contact with the skin surface; and correct the estimated blood perfusion rate based on the estimated thermal contact resistance.

6. The electronic device of claim 1, further comprising a photoplethysmography (PPG) sensor configured to measure a PPG signal of the user, wherein the processor is further configured to:

estimate an amount of heat generation by metabolism based on the PPG signal; and estimate the core body temperature of the user based on the first temperature, the estimated heat flux, the estimated blood perfusion rate, and the estimated amount of heat generation.

7. The electronic device of claim 1, wherein each of the first heating element and the second heating element are formed in a multi-layer structure.

8. The electronic device of claim 7, wherein the processor is further configured to operate the first heating element and the second heating element independently of each other.

9. The electronic device of claim 1, wherein at least one of the first temperature sensor and the second temperature sensor is a contact type temperature sensor.

10. The electronic device of claim 1, wherein the first temperature sensor is disposed at a center of a first end of the main body, and the second temperature sensor is disposed at a center of a second end of the main body.

11. The electronic device of claim 1, further comprising a display configured to provide the user with the estimated core body temperature of the user.

* * * * *